United States Patent
Mochizuki et al.

(10) Patent No.: US 6,187,763 B1
(45) Date of Patent: Feb. 13, 2001

(54) ACTIVATED VITAMIN $D_3$ EMULSION-TYPE LOTIONS

(75) Inventors: Seiji Mochizuki; Wataru Akasofu; Katsumi Sakurai; Kazuya Takanashi; Noriaki Okamura; Takao Fujii, all of Hino (JP)

(73) Assignee: Teijin Limited, Osaka (JP)

( * ) Notice: Under 35 U.S.C. 154(b), the term of this patent shall be extended for 0 days.

(21) Appl. No.: 09/423,230

(22) PCT Filed: Mar. 3, 1999

(86) PCT No.: PCT/JP99/01025

§ 371 Date: Feb. 1, 2000

§ 102(e) Date: Feb. 1, 2000

(87) PCT Pub. No.: WO99/44617

PCT Pub. Date: Sep. 10, 1999

(30) Foreign Application Priority Data

Mar. 4, 1998 (JP) .................................................. 10-052019

(51) Int. Cl.⁷ .................................................. A61K 31/593
(52) U.S. Cl. .............................................................. 514/167
(58) Field of Search ............................................... 514/167

(56) References Cited

FOREIGN PATENT DOCUMENTS

| | | |
|---|---|---|
| 4-230317 | 8/1992 | (JP) . |
| 7-291868 | 11/1995 | (JP) . |
| 9-249555 | 9/1997 | (JP) . |
| WO 95/06482 | 3/1995 | (WO) . |

*Primary Examiner*—Barbara Badio
(74) *Attorney, Agent, or Firm*—Sughrue, Mion, Zinn, Macpeak & Seas, PLLC

(57) ABSTRACT

The present invention provides a pharmaceutical composition for local administration in the form of an emulsion that contains active vitamin $D_3$ and is suitable for application to areas with (the) hair, while also having satisfactory pharmacological activity, primary drug stability and physical stability. This lotion contains (a) a therapeutically effective amount of active vitamin $D_3$, (b) an oil phase component containing a solid oil component comprising white Petrolatum and a higher alcohol and a liquid oil component comprising squalane, (c) an aqueous phase component containing ionic polysaccharide, and (d) nonionic surfactant; wherein, (1) the content of said ionic polysaccharide is 0.3–1.0 parts by weight of the entire preparation, (2) the content of said higher alcohol is 0.2–1.0 parts by weight of the entire preparation, and (3) the HLB of said nonionic surfactant is 10 or more.

8 Claims, 2 Drawing Sheets

US 6,187,763 B1

ACTIVATED VITAMIN $D_3$ EMULSION-TYPE LOTIONS

FIELD OF THE INVENTION

The present invention relates to an active vitamin $D_3$ emulsion lotion, and more particularly, to an active vitamin $D_3$ emulsion lotion comprising a specific oil phase component, a specific aqueous phase component, and a nonionic surfactant; wherein, a ionic polysaccharide contained in the aqueous phase component is of a specific content, a higher alcohol contained in the oil phase component is of a specific content, and an HLB of said nonionic surfactant is of a specific value.

BACKGROUND ART

Since, for example, 1α,25-dihydroxycholecalciferol or 1α,24-dihydroxycholecalciferol is a substance that exhibits Ca regulatory action known to be a physiological action of vitamin $D_3$, it is referred to as active vitamin $D_3$. Although the physiological action of active vitamin $D_3$ is diverse, probably regarding the differentiation inducing action and growth inhibitory action of active vitamin $D_3$, findings have been obtained which state that the active vitamin $D_3$ is effective against psoriasis which is a refractory skin disease, by a mechanism which normalizes the undifferentiation and accelerated growth of epidermal cells which are considered to be the cause of this disease (see T. Matsunaga, et al., J. Dermatol., Vol. 17, No. 3, p. 135 (1990)).

Since skin diseases such as psoriasis are diseases of the epidermal layer of the skin outer layer, local administration rather than systemic administration in the form of oral administration or injections and so forth is more advantageous in terms of bioavailability. Moreover, this type of administration is also preferable since it is possible to prevent systemic adverse side effects. Examples of drug forms for local administration include semi-solid preparations such as ointments and creams; liquid preparations such as lotions and liniments; tapes; poultices and powders. However, the semi-solid preparations or liquid preparations are preferred in consideration of the pathology of psoriasis.

Known examples of semi-solid preparations include an oily ointment having 1α,24-dihydroxyvitamin $D_3$ for its primary drug and white Petrolatum for its base (Japanese Examined Patent Publication No. 3-68009), a cream preparation containing an oil phase component comprising a viscosity adjuster such as cetyl alcohol and a lipophilic solubilizer such as liquid paraffin, a surfactant such as sorbitan monostearate (span 60), and an aqueous phase component such as propylene glycol (Japanese Unexamined Patent Publication No. 4-210903), and an O/W emulsion ointment having 1α,24-dihydroxyvitamin $D_3$ for its primary drug, and containing an oil phase component comprising a solid oil component such as white Petrolatum, a surfactant comprising sodium laurylsulfate, etc., and an aqueous phase component comprising propylene glycol, etc. (Japanese Examined Patent Publication No. 3-68009). In addition, an example of a known cream preparation has 1α,24-dihydroxyvitamin $D_3$ for its primary drug, and contains a solid oil component comprising white Petrolatum, etc., an oil phase component containing a liquid oil component comprising squalane, etc., a surfactant such as polyoxyethylene hydrogenated castor oil 60, and an aqueous phase component such as propylene glycol (specification of WO95/6482).

However, when considering the pathology of skin diseases, lotion preparations are preferable as preparations for local administration. Since roughly ⅓ of the patients in which psoriasis occurs on the scalp in particular have the hair, lotions are preferable which do not become sticky at locations where there is (the) hair, are easily applied, and have the optimum viscosity for inhibiting running (having a viscosity of 500 to 1400 mPa·s when measured with a Brookfield rotational viscometer using a spindle no. LV4, at 60 rpm and 25° C). In addition, it is desirable that this viscosity not be easily affected by external stimulation such as temperature or vibrations so that it remains constant at all times. Moreover, since the pathology of psoriasis involves an abnormality in which epidermal cells of the skin are destroyed, and since it is predicted that there is weak resistance to irritating substances, it is preferable that preparations used for psoriasis have a low level of irritation.

In general, lotions are roughly classified into solution-type lotions and emulsion-type lotions.

Of active vitamin $D_3$ lotions, solution-type lotions of calcipotriol or 20(R)-22-oxa-vitamin $D_3$ derivative are disclosed in the specification of WO91/12807 and the specification of WO92/01454. Since these lotions use a solvent such as ethanol giving a low viscosity to the lotion, not only do they run easily when applied preventing the preparation from effectively remaining at the affected area, but also when applied to the hairline on the forehead, there is a problem of the preparation getting into the eyes. In addition, there is also concern over the irritability of organic solvents such as ethanol used as solvent or absorption enhancer.

An example of a emulsion-type lotion is described, for example, in Japanese Unexamined Patent Publication No. 60-174705, and is composed of active vitamin $D_3$ and its derivatives, an oil phase component such as spermaceti wax, cetanol, Petrolatum or squalane, a surfactant such as polyoxyethylene (10 mol) monostearate or sorbitan monooleate, and an aqueous phase component such as glycerin. In addition, an emulsion-type lotion is also disclosed in Japanese Examined Patent Publication No. 3-68009 that contains 1α,24-dihydroxyvitamin $D_3$, an oil phase component comprising a solid oil component such as stearyl alcohol and a liquid oil component such as liquid paraffin, and a surfactant comprising sodium laurylsulfate.

If these emulsion-type lotions are, for example, stored in an environment of 50° C. or lower or stimulated by vibration, a change in viscosity occurs and the gelation is observed.

Namely, conventional active vitamin $D_3$ emulsion lotions are not always satisfactory with respect to the point of pharmacological activity and chemical stability of the primary drug, the point of having optimum viscosity with respect to, for example, not sticking to areas of (the) hair, being easily applied and not running easily, the point of feel during application, and the point of physical stability of the preparation when subjected to long-term storage, heat or vibrations etc.

DISCLOSURE OF THE INVENTION

Namely, the object of the present invention is to provide an active vitamin $D_3$ emulsion lotion in which the pharmacological activity and chemical stability of the primary drug in the form of active vitamin $D_3$ are retained.

Moreover, another object of the present invention is to provide an active vitamin $D_3$ emulsion lotion that retains the pharmacological activity and chemical stability of the primary drug in the form of active vitamin $D_3$, and/or has excellent pharmacological activity and chemical stability, and has a viscosity suitable for application to, for example, areas of (the) hair.

Moreover, still another object of the present invention is to provide an active vitamin D3 emulsion lotion that retains the pharmacological activity and chemical stability of the primary drug in the form of active vitamin $D_3$, and/or has excellent pharmacological activity and chemical stability, has a viscosity suitable for application to, for example, areas of (the) hair, has excellent physical stability with respect to subjecting the preparation to long-term storage, heat or vibrations, and has a low level of skin irritability.

In consideration of the above-mentioned objects, as a result of conducting earnest studies to develop an active vitamin $D_3$ oil-in-water (O/W) type of emulsion lotion that satisfies the conditions of (1) not sticking, being easily applied and having a viscosity that prevents running even when applied to areas of (the) hair, (2) retaining pharmacological activity and chemical stability of active vitamin $D_3$ sufficient for use as a pharmaceutical, (3) having sufficient physical stability for use as a pharmaceutical, and (4) having a low level of irritability to the skin, the inventors of the present invention found that the above-mentioned objects can be achieved by combining the use of a specific oil phase component, the addition of an ionic polysaccharide to an aqueous phase component, the use of a nonionic surfactant, as well as the use of the specific content of said ionic surfactant, the specific content of a higher alcohol in the oil phase component and of the specific HLB of said nonionic surfactant, thereby leading to completion of the present invention.

Namely, the present invention provides an active vitamin $D_3$ emulsion lotion, for example for treatment of skin disease, containing:
- (a) a therapeutically effective amount of active vitamin $D_3$,
- (b) an oil phase component containing a solid oil component comprising white Petrolatum and a higher alcohol, and a liquid oil component comprising squalane,
- (c) an aqueous phase component containing ionic polysaccharide, and
- (d) nonionic surfactant; wherein,
    - (1) the content of said ionic polysaccharide is 0.3 to 1.0 parts by weight of the entire preparation,
    - (2) the content of said higher alcohol is 0.2 to 1.0 parts by weight of the entire preparation, and
    - (3) the HLB of said nonionic surfactant is 10 or more.

MODE FOR CARRYING OUT THE INVENTION

Figure 1:
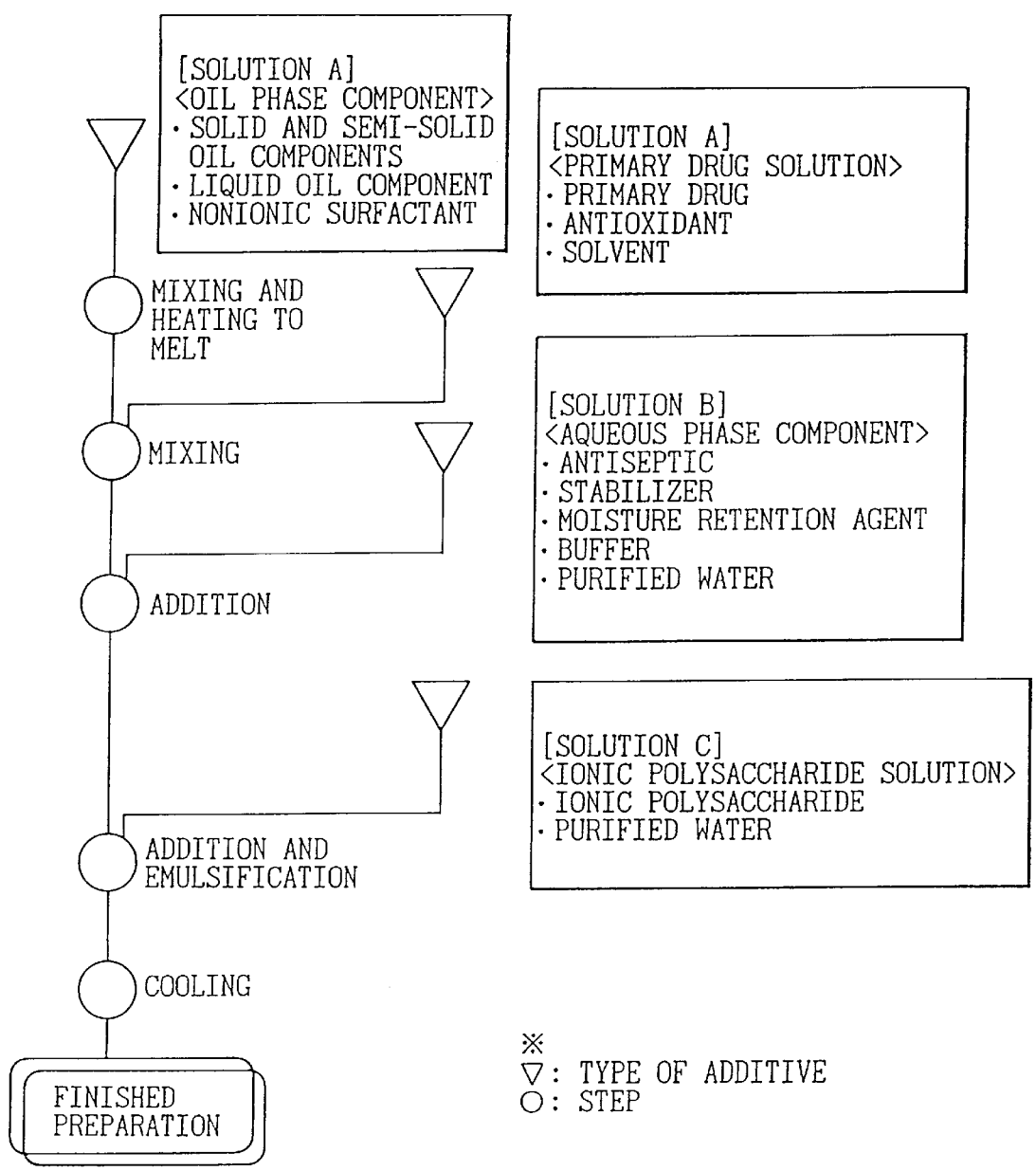
FIG. 1 is a flow chart indicating an example of the manufacturing process of lotions of the present invention.

The oil phase component that forms an active vitamin $D_3$ lotion of the present invention contains a solid oil component comprising white Petrolatum and higher alcohol, and a liquid oil component comprising squalane.

The white Petrolatum of the present invention is purified by decoloring a mixture of hydrocarbons obtained from petroleum, and the quality standards stipulated in, for example, the Japanese Pharmacopoeia, are used for its quality standards. In particular, the white Petrolatum having high purity is preferable for the stability of active vitamin $D_3$, for example, 1α,24-dihydroxyvitamin $D_3$, and that having, for example, a peroxide value of 0.5 or less is preferable.

In addition, the squalane of the present invention is a saturated hydrocarbon obtained by, for example, reducing hydrocarbons obtained from the liver oil of sharks residing deep in the ocean, and the quality standards stipulated in, for example, Japanese Cosmetic Raw Material Standards are used for its quality standards.

The hydrocarbon-based oil phase component described above has been confirmed to have lower irritability as compared with polar oil phase components such as fatty acid esters in a skin primary irritation test in rabbits conducted by the inventors of the present invention. The use of this oil phase component with a low level of irritability makes it possible to obtain a lotion having a low level of irritability and capable of be applied to the affected area of the skin such as in psoriasis.

Here, it is preferable that the higher alcohol content of the present invention be 0.2 to 1.0 parts by weight of the entire preparation. If the amount is greater than 1.0 parts by weight, it tends to be difficult to obtain a lotion that is free of changes in viscosity caused by the environment such as heat or vibrations. In addition, if the amount is less than 0.2 parts by weight, it becomes difficult to form a protective layer (phase D) around the oil phase. This results in greater susceptibility to the occurrence of phase separation of the oil and aqueous phases, eventually tending to significantly lower the chemical stability of the active vitamin $D_3$.

Here, a preferable example of the viscosity of the lotion of the present invention is a lotion viscosity of 500 to 1400 mPa·s when measured with a Brookfield rotational viscometer using a spindle no. LV4, at 60 rpm and 25° C.

More specifically, the contents of the white Petrolatum, higher alcohol and squalane that form the oil phase component of the present invention preferably form a solid oil component comprising 2 to 5 parts by weight of white Petrolatum and 0.2 to 0.5 parts by weight of higher alcohol, and a liquid oil component comprising 1 to 2.5 parts by weight of squalane within a range that satisfies the above-mentioned weight ratio of the solid oil component and liquid oil component.

In addition to white Petrolatum, higher alcohol and squalane as mentioned above, other solid oil and liquid oil components may be added to the oil phase component of the present invention. Examples of solid oil components include solid paraffin, spermaceti wax and beeswax. Their added amounts should be within the range that allows one of the objects of the present invention, for example physical stability, to be maintained. As examples of the amounts added, an amount of ¼ the parts by weight or less of the solid oil component of the present invention is preferable for being able to maintain the viscosity of a lotion that is suitable for application to sites where there is (the) hair. Examples of the liquid oil component include esters such as medium chain fatty acid triglycerides, diisopropyladipate and isopropylmyristate, liquid paraffin, and dimethylpolysiloxane. The amounts of these liquid oil components added should be within the range in which one of the objects of the present invention, for example physical stability, is maintained. For example, an amount of ½ the parts by weight or less of the squalane of the present invention is preferable for being able to maintain the viscosity of a lotion suitable for application to sites where there is (the) hair. In addition, with respect to irritability, it was found that using an oil phase component other than a hydrocarbon-based oil phase component results in slightly greater irritability than the use of a hydrocarbon-based oil phase component.

Antioxidant can be added to the oil phase component of the present invention. Examples of antioxidants include butylhydroxytoluene, butylhydroxyanisol and dl-α-tocopherol, while dl-α-tocopherol is added preferably. The amount of said antioxidants is normally 0.001 to 2.0 parts by weight, and more preferably 0.01 to 1.0 parts by weight.

The aqueous phase component of the present invention contains ionic polysaccharide at a specified concentration. Furthermore, an ionic polysaccharide in the present invention refers to a polysaccharide in which the sugar chain has, for example, a carboxyl group or sulfate group, and has a sugar chain structure that is ionized in aqueous solution. As a result of containing an ionic polysaccharide, the emulsion lotion of the present invention is hardly affected at all by changes in viscosity caused by external stimuli such as heat or vibrations. In addition, it also serves to stabilize the emulsion by preventing phase separation. In addition, even in the case in which active vitamin $D_3$, the primary drug of the present invention, is unstable in water as with 1α,24-dihydroxyvitamin $D_3$, there is the effect of preventing impairment of the stability of the primary drug.

Examples of ionic polysaccharide include xanthane gum and/or carrageenan, while xanthane gum is preferable. The content of these ionic polysaccharides is preferably 0.3 to 1.0 parts by weight of the entire preparation, and more preferably 0.4 to 0.8 parts by weight.

In addition, moisture retention agent, antiseptic, chelating agent, buffer and so forth can be added to the aqueous phase component. Examples of moisture retention agents include propylene glycol, glycerin and sorbitol, and the amount is 1 to 20 parts by weight, and preferably 2 to 15 parts by weight. Examples of antiseptics include parabens such as methylparaben, propylparaben and their mixtures, chlorobutanol, monothioglycerol, sorbic acid, potassium sorbate and benzyl alcohol, and the added amount is 0.001 to 10.0 parts by weight, and preferably 0.01 to 5.0 parts by weight. Examples of chelating agents include citric acid, sodium citrate and sodium edetate, and the amount is 0.001 to 5.0 parts by weight, and preferably 0.01 to 3.0 parts by weight. Examples of buffers include disodium hydrogenphosphate, sodium dihydrogenphosphate and potassium dihydrogenphosphate, and they are added in the required weight ratio for adjusting the pH of the aqueous phase component to 6.5 to 8.5.

In the lotion of the present invention, the weight ratio of the above-mentioned oil phase component and aqueous phase component (oil phase component/aqueous phase component) is 15/85 to 3/97. If the ratio is outside this range, the previously indicated viscosity and stability preferable for use as a lotion cannot be obtained.

The active vitamin $D_3$ lotion of the present invention also contains nonionic surfactant. This nonionic surfactant is comprised of two or more types of surfactants. Examples of such surfactants of the present invention include one or more types of surfactants selected from the group consisting of low HLB surfactants such as sorbitan monooleate, sorbitan monostearate, sorbitan sesquioleate, sorbitan trioleate, glyceryl monostearate, glyceryl monooleate and propylene glycol monostearate, and high HLB surfactants such as polyoxyethylene (30, 40 or 60) sorbitotetraoleate, polyoxyethylene hydrogenated castor oil 60 hardened castor oil, sorbitan monolaurate, sorbitan monopalmitate, polyoxyethylene (20) sorbitan monolaurate, polyoxyethylene (20) sorbitan monopalmitate, polyoxyethylene (20) sorbitan monostearate, polyoxyethylene (20) sorbitan monooleate, polyoxyethylene (10) monolaurate and polyoxyethylene (23, 25 or 30) cetyl ether. Normally, a low HLB surfactant is combined with a high HLB surfactant to adjust HLB for the purpose of stabilizing the emulsion.

The content of nonionic surfactant of the present invention is preferably 1.8 to 5.2 parts by weight of the entire preparation. Moreover, in this case, it is preferable that the HLB of the overall nonionic surfactant be 10 or more, and preferably 11.0 or more to allow the above-mentioned ionic polysaccharide to demonstrate its phase separation preventive effect. More preferably, the overall content of nonionic surfactant is about 11.5 to 14.5.

Examples of active vitamin $D_3$ of the present invention include active vitamin $D_3$ selected from the group consisting of 1α,24-dihydroxyvitamin $D_3$, 1α,25-dihydroxyvitamin $D_3$ and 1α-hydroxyvitamin $D_3$. 1α,24(R)-dihydroxyvitamin $D_3$ and 1α,24(S)-dihydroxyvitamin $D_3$ are preferable, while 1α,24(R)-dihydroxyvitamin $D_3$ is particularly preferable due to its excellent pharmacological activity. In addition, crystals of 1α,24(R)-dihydroxyvitamin $D_3$ are preferable in terms of purity, and, for example, its 1 hydrate form can be used.

The amount of active vitamin $D_3$ of the present invention is the dose that is effective for treating the skin disease for which it is applied, and normally is within the range of about 0.00005 to 0.01 parts by weight as the concentration in the lotion.

The active vitamin $D_3$ lotion of the present invention is produced in accordance with routine methods by dissolving a required amount of active vitamin $D_3$ in an oil phase component with surfactant with heating; mixing the solution with the aqueous phase component or aqueous phase component excluding the ionic polysaccharide solution, that has been heated in an emulsifing machine; emulsifying the mixture to form a uniform emulsion, or adding the ionic polysaccharide solution to the mixture as necessary and then emulsifying the mixture to form a uniform emulsion; and finally cooling.

The active vitamin $D_3$ lotion of the present invention can be used as a therapeutic agent for skin diseases such as psoriasis vulgaris, pustular psoriasis, psoriasis guttata, erythrodermal psoriasis, psoriasis arthopica, psoriasis gravis and other types of psoriasis and keratosis. Although the dosage varies according to the severity of the disease and so forth, it is preferable, for example, to administer a lotion having a concentration of 1α,24-dihydroxyvitamin $D_3$ of 100 to 0.1 μg/g of lotion once to several times daily to the affected area.

Thus, an emulsion lotion is provided that contains active vitamin $D_3$, has a viscosity that is suitable for application to a site where there is (the) hair, has satisfactory pharmacological activity, stability of the primary drug and physical stability, and has a low level of skin irritability. In addition, the significance of providing this active vitamin $D_3$ emulsion lotion for the clinical setting is extremely great.

EXAMPLES

Although the following provides a further explanation of the present invention through its examples, it goes without saying that the present invention is by no means limited to these examples. An explanation is first provided regarding the various types of test methods used in the examples.

Summary of Description and Purposes of Testing

The contents and purposes of tests performed are described in Table 1.

TABLE 1

Contents and Purposes of Tests Performed

| Test No. | Description | Purpose |
|---|---|---|
| Test Method 1 | Location viscosity evaluation test Measurement of viscosity using a rotational viscometer | Evaluation of viscosity |
| Reference Test 1 | Evaluation of viscosity by a sensory test | Determination of optimum viscosity range |
| Test Method 2 2-1 | Lotion physical stability tests Gravitational load test (centrifugal phase separation test) | Evaluation of physical stability of emulsion according to presence of phase separation or gelation |
| 2-2 | Thermal load test (storage at 40 to 50° C.) | |
| Test Method 3 | Lotion primary drug chemical stability test Measurement of primary drug residual rate by HPLC (storage at 40 to 50° C.) | Evaluation of chemical stability |
| Test Method 4 | Lotion pharmacological activity test ODC inhibitory activity test | Evaluation of pharmacological activity of preparation |
| Test Method 5 | Lotion skin irritation test Comparative cumulative skin irritation test using rabbits | Evaluation of safety (irritability) of preparation |

The following provides a detailed description of the test methods relating to Table 1.

Test Method 1: Lotion Viscosity Test Method

A sample lotion was filled into glass screw-top tube (Maruem, No. 3L) having a diameter of 21 mm, mouth diameter of 12 mm and depth of 50 mm up to the threads so as not to allow entrance of bubbles. Testing was performed in an environment at 25° C. under the following conditions in compliance with the provisions of the Japanese Pharmacopoeia General Test Methods, Viscosity Measurement Method, Method No. 2: Rotational Viscometer Method.

Test Conditions:

Apparatus: Single cylinder rotational viscometer DV-II+ (Brookfield)

Rotor: LV4 rotor

Speed: 60 rpm

Measurement: Viscosity was measured after rotating the rotor for 3 minutes.

Evaluation criterion was based on taking a viscosity of 500 to 1400 mPa·s to be the optimum viscosity (see Reference Test 1).

Reference Test 1: Viscosity Evaluation of Lotion Using Sensory Tests

Stickiness and ease of application were evaluated by touch feeling, and resistance to running was evaluated visually for commercially available lotions and test lotions. Furthermore, the commercially available lotions were placed in and pushed out of the containers in which they are sold, while the test lotions were placed in polyethylene containers.

Evaluation criteria are shown in Table 2, while results are shown in Table 3.

TABLE 2

Viscosity Evaluation Standards Using Sensory Tests

| Evaluated Parameter | Evaluation Standards |
|---|---|
| Stickiness | +: Not sticky to the touch feeling and considered not to adhere to (the) hair assuming application to the head. |
| | −: sticky to the touch feeling and considered to easily adhere to (the) hair assuming application to the head. |
| Ease of application | +: Suitable spreadability and the amount pushed out of the container to be easily adjusted |
| | −: Excessive spreadability, considered to be difficult to retain at the affected area, or viscosity too high causing unevenness when pushed out of the container |
| Resistance to running | +: Little risk of entering the eyes due to running assuming application to the head. |
| | −: High risk of entering the eyes due to running assuming application to the head. |

TABLE 3

Evaluation of Viscosity by Sensory Tests

| Lotion | Viscosity (mPa · s) | Stickiness | Ease of application | Resistance to running | Evaluation |
|---|---|---|---|---|---|
| Commercial product A* | 80 | + | − | − | − |
| Commercial product B* | 270 | + | − | − | − |
| Commercial product C* | 590 | + | + | + | + |
| Commercial product D* | 760 | + | + | + | + |
| Test preparation A** | 1010 | + | + | + | + |
| Commercial product E* | 1140 | + | + | + | + |
| Test preparation B** | 1380 | + | + | + | + |
| Test preparation C** | 1520 | + | − | + | − |
| Test preparation D** | 1850 | − | − | + | − |

*Commercial products A through D were as indicated below.
Commercial Product A: Nippon Glaxo, Delmovate Scalp Lotion
Commercial Product B: Shionogi Pharmaceuticals, Rinderon V Lotion
Commercial Product C: Tanabe Pharmaceuticals, Topsym Lotion
Commercial Product D: Taisho Pharmaceuticals, Pandel Lotion
Commercial Product E: Kowa Shinyaku, Lidomex Lotion
**Test preparations A through D were as shown in Table 4.

TABLE 4

| Ingredient | Test A (Example 1) | Test preparation B | Test preparation C | Test preparation D |
|---|---|---|---|---|
| 1α,24-dihydroxyvitamin $D_3$ | 0.0002 | — | — | — |
| dl-α-tocopherol | 0.02 | — | — | — |
| Diisopropyladipate | 0.5 | 0.5 | 0.5 | 0.5 |
| White Petrolatum | 3.5 | — | — | 3.4 |
| Paraffin | 0.7 | 0.35 | 0.35 | 0.7 |
| Stearyl alcohol | 0.3 | 0.35 | 0.35 | 0.3 |
| Squalane | 1.7 | — | — | 1.7 |

TABLE 4-continued

| Ingredient | Test A (Example 1) | Test preparation B | Test preparation C | Test preparation D |
|---|---|---|---|---|
| Fatty acid triglyceride | — | 4.5 | 4.5 | — |
| Liquid paraffin | — | 5.0 | 5.0 | — |
| Glyceryl monostearate | 0.6 | 1.0 | 1.0 | 1.6 |
| Polyoxyethylene hydrogenated castor oil 60 | 1.0 | 1.0 | 1.0 | 0.5 |
| Polyoxyethylene (23) cetyl alcohol | 1.0 | 1.0 | 1.0 | 0.5 |
| Hydroxymethylbenzoate | 0.1 | 0.1 | 0.1 | 0.1 |
| Hydroxypropylbenzoate | 0.05 | 0.05 | 0.05 | 0.05 |
| Sodium citrate | 0.57 | 0.57 | 0.57 | 0.57 |
| Propylene glycol | 10 | 10 | — | 10 |
| Butylene glycol | — | — | 10 | — |
| Glycerol | — | — | — | — |
| Disodium hydrogenphosphate | Suitable amount | Suitable amount | Suitable amount | Suitable amount |
| Potassium dihydrogenphosphate | Suitable amount | Suitable amount | Suitable amount | Suitable amount |
| Hydroxyethylcellulose | — | — | 0.3 | — |
| Xanthane gum | 0.6 | 0.6 | 0.6 | 0.6 |
| Purified water | Suitable amount | Suitable amount | Suitable amount | Suitable amount |
| Total | 100 | 100 | 100 | 100 |
| HLB | 13 | 11.7 | 11.7 | 8 |

*Units: parts by weight
*Total parts by weight was adjusted with purified water.

According to the results of Table 2, the optimum viscosity for efficiently reaching the affected area, safety and easy handling as an externally applied medication for skin diseases that is applied to areas of (the) hair and so forth was found to be 500 to 1400 mPa·s.

Test Method 2: Lotion Physical Stability Test Methods 2-1 Gravitational Load Test One g of sample lotion was placed in a centrifuge tube and removed after centrifuging for 1 hour at about 3750 rpm. The appearance of the lotion was observed and checked for the presence of separation of the oil and aqueous phases.

The evaluation criteria were the absence of phase separation and spots.

2-2 Thermal Load Test (Heating Test)

Eight g of sample lotion was placed in a glass sample tube. The tube was sealed and then stored in a constant temperature bath at 50° C. or 40° C. Observation of lotion appearance and measurement of viscosity were performed over time, and the lotion was checked for the presence of separation between the oil and aqueous phases as well as for changes in viscosity.

The evaluation criteria were the absence of phase separation and spots.

Test Method 3: Lotion 1α,24-dihydroxyvitamin $D_3$ Chemical Stability Test Method 500 mg of lotion were placed in a centrifuge tube followed by the addition of 50 μl of internal standard (prednisolone 100 μg/ml) and 5 ml of dichloromethane, after which the sample was centrifuged for 10 minutes at 3000 rpm while cooling to 5° C. after shaking for 10 minutes. The bottom dichloromethane layer was removed, and a portion was injected into an HPLC to determine the amount of 1α,24-dihydroxyvitamin $D_3$. HPLC conditions were as described below.

Column: Inertsil SIL 4.6-250 mm
Column temperature: 40° C.
Eluent: n-hexane/EtOH (89/11)
Flow rate: 1 ml/min.
Detector: UV 265 nm Although the evaluation criterion is to judge a residual rate of the primary drug of 95% or more as being stable, in consideration of the measurement error (±2%), a residual rate of 93% or more was judged as being preferable.

Test Method 4: 1α,24-dihydroxyvitamin $D_3$ Lotion Pharmacological Activity Test Method The cell growth inhibitory activity of 1α,24-dihydroxyvitamin $D_3$ in a psoriasis animal model was evaluated using ODC (ornithine decarboxylase) activity as a marker of cell growth activity. Namely, epidermal cell growth was accelerated by treating the skin of hairless mice with TPA (12-O-tetradecanoylphorbol-13-acetate) followed by administration of 1α,24-dihydroxyvitamin $D_3$ lotion and measuring inhibition of cell growth in terms of ODC activity. More specifically, 10 nmol of TPA was first administered to a 3×3 $cm^2$ area of the backs of hairless mice in order to accelerate the growth of epidermal cells. Next, 50 mg of the test sample (lotion) was administered to animals of the dose group at the same site (lotion was not administered to animals of the control group). Five hours later, the skin of the administration site was excised and ODC activity was measured according to the method of Ciba, K., et al. (Cancer Res., 44: 1387–1391 (1984)). The ratio of ODC activity of the dose group to that of the control group was taken to represent the inhibition rate, which was in turn used as an indicator of the pharmacological activity of 1α,24-dihydroxyvitamin $D_3$ lotion.

The evaluation criterion is to be equivalent to Teijin Bonalpha Ointment (1,α24-dihydroxyvitamin $D_3$ ointment) which was previously marketed and has been used clinically. Furthermore, equivalency refers to that described in biological equivalency testing of Pharmaceutical Manufacturing Guidelines (Yakugyo Jihosha Publishing).

Test Method 5: Comparative Cumulative Skin Irritation Test Method in Rabbits 0.05 g of example and comparative example preparations were administered daily for 7 days (occlusive application) to an area of skin on the backs (6.25 $cm^2$) of Japanese white male rabbits followed by evaluation of cumulative irritability (rubor) of the skin according to Dray's evaluation method.

The evaluation criteria are shown in Table 5. Furthermore, preparations having a score of less than 1 in the results on day 7 were considered to have a low level of irritability.

TABLE 5

Evaluation Criteria of Comparative Cumulative Skin Irritation Test in Rabbits

| | Degree of Skin Reaction | Score |
|---|---|---|
| Erythema | No erythema | 0 |
| Scabbing | Very mild erythema (barely recognizable) | 1 |
| | Clear erythema | 2 |
| | Moderate to severe erythema | 3 |
| | Deep red, severe erythema, mild scab formation (impairment of deep tissue) | 4 |

TABLE 5-continued

Evaluation Criteria of Comparative Cumulative Skin Irritation Test in Rabbits

| | Degree of Skin Reaction | Score |
|---|---|---|
| Edema | No edema | 0 |
| | Very mild edema | 1 |
| | Clear edema | 2 |
| | Moderate edema (swelling of about 1 mm) | 3 |
| | Severe edema (swelling of more than 1 mm and spreading to surrounding area) | 4 |

Example 1

The composition prepared as Example 1 is shown in Table 6, while a summary of the production process is shown in FIG. 1.

TABLE 6

Composition of Example 1

| | | |
|---|---|---|
| Primary drug | 1. 1α,24-dihydroxyvitamin $D_3$ | 0.0002 ppw |
| Antioxidant | 2. dl-α-tocopherol | 0.02 ppw |
| Solvent | 3. Diisopropyladipate | 0.5 ppw |
| Solid oil component | 4. White Petrolatum | 3.5 ppw |
| | 5. Paraffin | 0.7 ppw |
| | 6. Stearyl alcohol | 0.3 ppw |
| Liquid oil component | 7. Squalane | 1.7 ppw |
| Nonionic surfactant | 8. Glyceryl monostearate | 0.6 ppw |
| | 9. Polyoxyethylene hydrogenated castor oil 60 | 1 ppw |
| | 10. Polyoxyethylene (23) cetyl alcohol | 1 ppw |
| Antiseptic | 11. Hydroxymethylbenzoate | 0.1 ppw |
| | 12. Hydroxypropylbenzoate | 0.05 ppw |
| Stabilizer | 13. Sodium citrate | 0.57 ppw |
| Moisture retention agent | 14. Propylene glycol | 10 ppw |
| Ionic polysaccharide | 15. Xanthane gum | 0.6 ppw |
| Buffer | 16. Disodium hydrogen-phosphate | Suitable (pH 7.5) |
| | 17. Sodium dihydrogen-phosphate | Suitable (pH 7.5) |
| Water | 18. Purified water | Suitable |
| Total | | 100 ppw |

Explanation of Preparation Method

The above-mentioned solid oil component (components 4 to 6), liquid oil component (component 7) and nonionic surfactant (components 8 to 10) were mixed and heated to 75 to 85° C. to form a uniform melt. A solution of 1α,24-dihydroxyvitamin $D_3$ (component 1) and antioxidant (component 2) in solvent (component 3) was added to the above mixture followed by heating to uniformly dissolve (Solution A). On the other hand, antiseptic (components 11 and 12), stabilizer (component 13), moisture retention agent (component 14) and buffer (components 16 and 17) were heated to 75–85° C. in purified water (component 18) to obtain a uniform solution (Solution B). Ionic polysaccharide (xanthane gum was used as ionic polysaccharide (component 15)) was dissolved in purified water to prepare ionic polysaccharide solution (Solution C).

Solutions A, B and C were mixed in a vacuum emulsifier (Mizuho) to emulsify and prepare the uniform primary emulsion. This was then cooled to room temperature to obtain a white lotion (Example 1).

Furthermore, the numbers described for each component shown in Table 2 may be used in place of the names of each component in Example 1 in the following examples and comparative examples. In addition, the examples and comparative examples described herein were prepared in compliance with the above-mentioned production method (FIG. 1) based on Example 1.

Examples 2 to 10 and Comparative Examples 1 to 10

A summary of the examples and comparative examples is shown in Table 7, while the compositions are shown in Tables 8 to 10.

TABLE 7

Summary of Examples 2 to 10 and Comparative Examples 1 to 10

| No. of Example, Comparative Example | Change in Composition from Example 1 | Resulting Findings |
|---|---|---|
| Comp. Ex. 1 | Amt. of xanthane gum: 0.6 → 0 ppw | Required amount of ionic polysaccharide |
| Comp. Ex. 2 | Amt. of xanthane gum: 0.6 → 0.2 ppw | Optimum amount range of ionic polysaccharide |
| Example 2 | Amt. of xanthane gum: 0.6 → 0.4 ppw | |
| Example 3 | Amt. of xanthane gum: 0.6 → 0.8 ppw | |
| Comp. Ex. 3 | Amt. of xanthane gum: 0.6 → 1.5 ppw | |
| Example 4 | Amt. of stearyl alcohol: 0.3 → 0 ppw | Required amount of stearyl alcohol |
| Comp. Ex. 4 | Amt. of stearyl alcohol: 0.3 → 0.2 ppw | Optimum amount range of stearyl alcohol |
| Example 5 | Amt. of stearyl alcohol: 0.3 → 1.0 ppw | |
| Comp. Ex. 5 | Amt. of stearyl alcohol: 0.3 → 1.2 ppw | |
| Comp. Ex. 6 | HLB: 13 → 8.2 | Optimum HLB |
| Example 6 | HLB: 13 → 10 | |
| Comp. Ex. 7 | HLB: 13 → 15 | |
| Example 7 | Oil phase/aqueous phase ratio: Approx. 10 → 6.5 ppw (surfactant also included in oil phase) | Optimum oil phase/aqueous phase ratio |
| Example 8 | Oil phase/aqueous phase ratio: Approx. 10 → 15 ppw (surfactant also included in oil phase) | |
| Comp. Ex. 8 | Oil phase/aqueous phase ratio: Approx. 10 → 30 ppw (surfactant also included in oil phase) | |
| Example 9 | Surfactant: 2.6 → 1.8 ppw | Allowed range of amount of surfactant |
| Example 10 | Surfactant: 2.6 → 5.2 | |
| Comp. Ex. 9 | Use of fatty acid ester in place of Petrolatum (HLB also changes) | Comparison of low irritability of oil phase component |
| Comp. Ex. 10 | Use of fatty acid ester and glycerol in place of Petrolatum (HBL also changes) | |

TABLE 8

Compositions of Examples and Comparative Examples
(Examples 1 to 3 and Comparative Examples 1 to 4)

| Component | Ex. 1 | Comp. Ex. 1 | Comp. Ex. 2 | Ex. 2 | Ex. 3 | Comp. Ex. 3 | Comp. Ex. 4 |
|---|---|---|---|---|---|---|---|
| 1α,24-dihydroxy-vitamin $D_3$ | 0.0002 | 0.0002 | 0.0002 | 0.0002 | 0.0002 | 0.0002 | 0.0002 |
| dl-α-tocopherol | 0.02 | 0.02 | 0.02 | 0.02 | 0.02 | 0.02 | 0.02 |
| Diisopropyladipate | 0.5 | 0.5 | 0.5 | 0.5 | 0.5 | 0.5 | 0.5 |
| White Petrolatum | 3.5 | 3.5 | 3.5 | 3.5 | 3.5 | 3.5 | 3.5 |
| Paraffin | 0.7 | 0.7 | 0.7 | 0.7 | 0.7 | 0.7 | 0.7 |
| Stearyl alcohol | 0.3 | 0.3 | 0.3 | 0.3 | 0.3 | 0.3 | 0 |
| Squalane | 1.7 | 1.7 | 1.7 | 1.7 | 1.7 | 1.7 | 1.7 |
| Glycerylmono-stearate | 0.6 | 0.6 | 0.6 | 0.6 | 0.6 | 0.6 | 0.6 |
| Polyoxyethylene hydrogenated castor oil 60 | 1.0 | 1.0 | 1.0 | 1.0 | 1.0 | 1.0 | 1.0 |
| Polyoxyethylene (23) cetyl alcohol | 1.0 | 1.0 | 1.0 | 1.0 | 1.0 | 1.0 | 1.0 |
| Hydroxymethyl-benzoate | 0.1 | 0.1 | 0.1 | 0.1 | 0.1 | 0.1 | 0.1 |
| Hydroxypropyl-benzoate | 0.05 | 0.05 | 0.05 | 0.05 | 0.05 | 0.05 | 0.05 |
| Sodium citrate | 0.57 | 0.57 | 0.57 | 0.57 | 0.57 | 0.57 | 0.57 |
| Propylene glycol | 10 | 10 | 10 | 10 | 10 | 10 | 10 |
| Disodium hydrogen-phosphate | Suitable amount | Suitable amount | Suitable amount | Suitable amount | Suitable amount | Suitable amount | Suitable amount |
| Potassium dihydrogen-phosphate | Suitable amount | Suitable amount | Suitable amount | Suitable amount | Suitable amount | Suitable amount | Suitable amount |
| xanthane gum | 0.6 | 0 | 0.2 | 0.4 | 0.8 | 1.5 | 0.6 |
| Purified water | Suitable amount | Suitable amount | Suitable amount | Suitable amount | Suitable amount | Suitable amount | Suitable amount |
| Total | 100 | 100 | 100 | 100 | 100 | 100 | 100 |
| HLB | 13 | 13 | 13 | 13 | 13 | 13 | 13 |

*Units: Parts by weight
*Total parts by weight was adjusted with purified water.

TABLE 9

Compositions of Examples and Comparative Examples
(Examples 1 and 4 to 6 and Comparative Examples 5 to 7)

| Component | Ex. 1 | Ex. 4 | Ex. 5 | Comp. Ex. 5 | Comp. Ex. 6 | Ex. 6 | Comp. Ex. 7 |
|---|---|---|---|---|---|---|---|
| 1α,24-dihydroxy-vitamin $D_3$ | 0.0002 | 0.0002 | 0.0002 | 0.0002 | 0.0002 | 0.0002 | 0.0002 |
| dl-α-tocopherol tocopherol | 0.02 | 0.02 | 0.02 | 0.02 | 0.02 | 0.02 | 0.02 |
| Diisopropyladipate | 0.5 | 0.5 | 0.5 | 0.5 | 0.5 | 0.5 | 0.5 |
| White Petrolatum | 3.5 | 3.5 | 3.5 | 3.5 | 3.5 | 3.5 | 3.5 |
| Paraffin | 0.7 | 0.7 | 0.7 | 0.7 | 0.7 | 0.7 | 0.7 |
| Stearyl alcohol | 0.3 | 0.2 | 1.0 | 1.2 | 0.3 | 0.3 | 0.3 |
| Squalane | 1.7 | 1.7 | 1.7 | 1.7 | 1.7 | 1.7 | 1.7 |
| Glycerylmono-stearate | 0.6 | 0.6 | 0.6 | 0.6 | 1.56 | 1.2 | 0.2 |
| Polyoxyethylene hydrogenated castor oil 60 | 1.0 | 1.0 | 1.0 | 1.0 | 0.52 | 0.7 | 1.2 |
| Polyoxyethylene (23) cetyl alcohol | 1.0 | 1.0 | 1.0 | 1.0 | 0.52 | 0.7 | 1.2 |
| Hydroxymethyl-benzoate | 0.1 | 0.1 | 0.1 | 0.1 | 0.1 | 0.1 | 0.1 |
| Hydroxypropyl-benzoate | 0.05 | 0.05 | 0.05 | 0.05 | 0.05 | 0.05 | 0.05 |
| Sodium citrate | 0.57 | 0.57 | 0.57 | 0.57 | 0.57 | 0.57 | 0.57 |
| Propylene glycol glycol | 10 | 10 | 10 | 10 | 10 | 10 | 10 |
| Disodium hydrogen-phosphate | Suitable amount | Suitable amount | Suitable amount | Suitable amount | Suitable amount | Suitable amount | Suitable amount |
| Potassium dihydrogen-phosphate | Suitable amount | Suitable amount | Suitable amount | Suitable amount | Suitable amount | Suitable amount | Suitable amount |
| Xanthane gum | 0.6 | 0.6 | 0.6 | 0.6 | 0.6 | 0.6 | 0.6 |

TABLE 9-continued

Compositions of Examples and Comparative Examples
(Examples 1 and 4 to 6 and Comparative Examples 5 to 7)

| Component | Ex. 1 | Ex. 4 | Ex. 5 | Comp. Ex. 5 | Comp. Ex. 6 | Ex. 6 | Comp. Ex. 7 |
|---|---|---|---|---|---|---|---|
| Purified water | Suitable amount | Suitable amount | Suitable amount | Suitable amount | Suitable amount | Suitable amount | Suitable amount |
| Total | 100 | 100 | 100 | 100 | 100 | 100 | 100 |
| HLB | 13 | 13 | 13 | 13 | 8.2 | 10 | 15 |

*Units: Parts by weight
*Total parts by weight was adjusted with purified water.

TABLE 10

Compositions of Examples and Comparative Examples
(Examples 1 and 7 to 10 and Comparative Examples 8 to 10)

| Component | Ex. 1 | Ex. 7 | Ex. 8 | Comp. Ex. 8 | Ex. 9 | Ex. 10 | Comp. Ex. 9 | Comp. Ex. 10 |
|---|---|---|---|---|---|---|---|---|
| 1a,24-dihydroxy-vitamin $D_3$ | 0.0002 | 0.0002 | 0.0002 | 0.0002 | 0.0002 | 0.0002 | 0.0002 | 0.0002 |
| di-α-tocopherol | 0.02 | 0.01 | 0.03 | 0.06 | 0.02 | 0.02 | 0.02 | 0.02 |
| Diisopropyladipate | 0.5 | 0.35 | 0.75 | 1.5 | 0.5 | 0.5 | 0.5 | 0.5 |
| White Petrolatum | 3.5 | 2.4 | 5.25 | 10.5 | 3.5 | 3.5 | — | — |
| Paraffin | 0.7 | 0.5 | 1.05 | 2.1 | 0.7 | 0.7 | 0.35 | 0.35 |
| Stearyl alcohol | 0.3 | 0.2 | 1.5 | 0.9 | 0.3 | 0.3 | 0.35 | 0.35 |
| Squalane | 1.7 | 1.2 | 2.55 | 5.1 | 1.7 | 1.7 | 1.7 | 1.7 |
| Fatty acid triglyceride | — | — | — | — | — | — | 4.5 | 4.5 |
| Liquid paraffin | — | — | — | — | — | — | 5.0 | 5.0 |
| Glycerylmono-stearate | 0.6 | 0.42 | 0.9 | 1.8 | 0.42 | 1.2 | 1.0 | 1.0 |
| Polyoxyethylene hydrogenated castor oil 60 | 1.0 | 0.69 | 1.5 | 3.0 | 0.69 | 2.0 | 1.0 | 1.0 |
| Polyoxyethylene (23) cetyl alcohol | 1.0 | 0.69 | 1.5 | 3.0 | 0.69 | 2.0 | 1.0 | 1.0 |
| Hydroxymethyl-benzoate | 0.1 | 0.1 | 0.1 | 0.1 | 0.1 | 0.1 | 0.1 | 0.1 |
| Hydroxypropyl-benzoate | 0.05 | 0.05 | 0.05 | 0.05 | 0.05 | 0.05 | 0.05 | 0.05 |
| Sodium citrate | 0.57 | 0.57 | 0.57 | 0.57 | 0.57 | 0.57 | 0.57 | 0.57 |
| Propylene glycol | 10 | 10 | 10 | 10 | 10 | 10 | 10 | 4 |
| Glycerin | — | — | — | — | — | — | — | 6 |
| Disodium hydrogen-phosphate | Suitable amount | Suitable amount | Suitable amount | Suitable amount | Suitable amount | Suitable amount | Suitable amount | Suitable amount |
| Potassium dihydrogen-phosphate | Suitable amount | Suitable amount | Suitable amount | Suitable amount | Suitable amount | Suitable amount | Suitable amount | Suitable amount |
| Xanthane gun | 0.6 | 0.6 | 0.6 | 0.6 | 0.6 | 0.6 | 0.6 | 0.6 |
| Purified water | Suitable amount | Suitable amount | Suitable amount | Suitable amount | Suitable amount | Suitable amount | Suitable amount | Suitable amount |
| Total | 100 | 100 | 100 | 100 | 100 | 100 | 100 | 100 |
| HLB | 13 | 13 | 13 | 13 | 13 | 13 | 11.7 | 11.7 |

*Units: Parts by weight
*Total parts by weight was adjusted with purified water.

Physical and Chemical Stability Tests

The physical stability of the lotions of Examples 1 through 10 and Comparative Examples 1 through 10 was determined by test methods 1 and 2, while their chemical stability was determined by test method 3. The evaluation criteria are shown in Table 11, and the results are shown in Table 12.

TABLE 11

Physical and Chemical Stability Test Evaluation Criteria

| Test Parameter | Evaluation Criteria |
| --- | --- |
| Viscosity Test | +: Viscosity within the range of 500 to 1400 mPa · s when measured according to test method 1. |
| | −: Viscosity less than or greater than 500 to 1400 mPa · s when measured according to test method 1. |
| Gravitational Load Test | +: No visual observation of phase separation |
| | −: Visual observation of phase separation and spots |
| Thermal Load Test Phase Separation | +: No visual observation of phase separation when stored at the temperature and for the duration described in Table 7-2. |
| | −: Visual observation of phase separation and spots when stored at the temperature and for the duration described in Table 7-2. |
| Viscosity Change | +: No visual observation of gelation when stored at the temperature and for the duration described in Table 7-2, and viscosity no greater than 1400 mPa · s when measured according to test method 1. |
| | −: Visual observation of gelation when stored at the temperature and for the duration described in Table 7-2, and viscosity greater than 1400 mPa · s when measured according to test method 1. |
| Primary Drug Residual Ratio | +: Judged to be stable if residual ratio of primary drug is at least 93% when stored at the temperature and duration described in Table 12, and measured according to test method 3. |
| | −: Judged to be unstable if residual ratio of primary drug is at least 93% when stored at the temperature and duration described in Table 12, and measured according to test method 1. |
| Overall Evaluation | +: Judged to be able to maintain physical and chemical stability as a pharmaceutical. |
| | −: Judged to be difficult to retain physical and chemical stability as a pharmaceutical. |

TABLE 12

Physical and Chemical Stability Results

| | | Physical Stability | | | | | Chemical Stability | | |
| | | Grav. Load Test | Thermal Load Test | | | | Thermal Load Test | | |
| | | | 50° C., 2 weeks | | 40° C., 3 mos. | | 50° C., 2 wks. | 40° C., 3 mos. | |
| Test Parameter | Test Viscosity | 3750 rpm Phase sep. | Phase sep. | Visc. change | Phase sep. | Visc. change | Primary Drug Residual Ratio (%) | | Overall Evaluation |
| --- | --- | --- | --- | --- | --- | --- | --- | --- | --- |
| Ex. 1 | + | + | + | + | + | + | 95 | 99 | + |
| Comp. Ex. 1 | − | − | − | + | − | + | 90 | 95 | − |
| Comp. Ex. 2 | − | − | − | + | + | + | 92 | 95 | − |
| Ex. 2 | + | + | + | + | + | + | 94 | 97 | + |
| Ex. 3 | + | + | + | + | + | + | 94 | 97 | + |
| Comp. Ex. 3 | − | + | + | + | + | + | 93 | 96 | − |
| Comp. Ex. 4 | + | + | − | + | + | + | 85 | 92 | − |
| Ex. 4 | + | + | + | + | + | + | 93 | 97 | + |
| Ex. 5 | + | + | + | + | + | + | 94 | 98 | + |
| Comp. Ex. 5 | + | + | + | + | + | − | 93 | 96 | − |
| Comp. Ex. 6 | + | − | − | + | − | + | 90 | 94 | − |
| Ex. 6 | + | + | + | + | + | + | 95 | 98 | + |
| Comp. Ex. 7 | + | − | − | + | − | + | 91 | 95 | − |
| Ex. 7 | + | + | + | + | + | + | 93 | 96 | + |
| Ex. 8 | + | + | + | + | + | + | 93 | 98 | + |
| Comp. Ex. 8 | + | − | − | + | − | + | 95 | 99 | − |
| Ex. 9 | + | + | + | + | + | + | 93 | 94 | + |
| Ex. 10 | + | + | + | + | + | + | 93 | 96 | + |
| Comp. Ex. 9 | + | + | + | + | + | + | 94 | 98 | + |
| Comp. Ex. 10 | + | + | + | + | + | + | 94 | 98 | + |

According to Table 12, those lotions that were judged to be acceptable in the gravitational load and thermal load tests conducted to examine physical stability were Examples 1 through 10 and Comparative Examples 9 and 10. Based on these findings, it was determined that physically stable lotion is obtained due to the synergistic effects of the three factors consisting of weight ratio of higher alcohol, weight ratio of xanthane gum, and HLB of the surfactant.

In addition, it was also determined that those lotion compositions in which phase separation occurred exhibited very poor chemical stability of 1α,24-dihydroxyvitamin $D_3$ and were unable to maintain stability as a pharmaceutical.

Furthermore, Comparative Examples 9 and 10 were found to be undesirable in the skin irritation test described below.

Pharmacological Activity Test of Lotion of Example 1

The results of conducting pharmacological activity tests on the lotion of Example 1 (although the 1α,24-dihydroxyvitamin $D_3$ content in the location was 2 μg/g) and the Bonalpha Ointment of Teijin (active 1α,24-dihydroxyvitamin $D_3$ ointment in which the content of 1α,24-dihydroxyvitamin $D_3$ in the ointment was 2 μg/g) according to test method 4 are shown in Table 13.

TABLE 13

Comparison of ODC Activity Inhibition Ratio of Example 1 and Ointment

| Composition | ODC Activity Inhibition Rate |
| --- | --- |
| Example 1 | 26% |
| Ointment | 26% |

Based on Table 13, the lotion of the present invention (Example 1) was determined to exhibit 1α,24-dihydroxyvitamin $D_3$ pharmacological activity equal to that of the ointment in an animal model of psoriasis.

Skin Irritation Test of Lotion of Example 1

Figure 2:
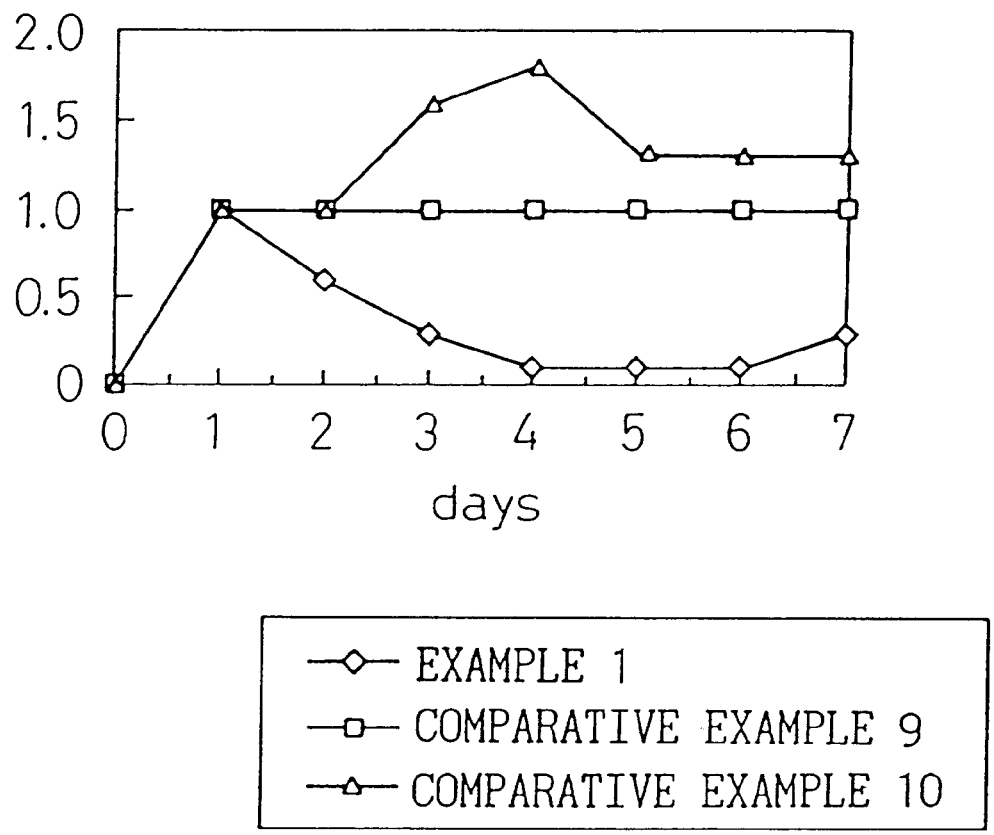
FIG. 2 is a graph showing the results of a cumulative skin irritation test in rabbits for the lotion of Example 1 of the present invention and the lotions of Comparative Examples 9 and 10.

The results of conducting a comparative cumulative skin irritation test in rabbits on the lotion of Example 1 (although the content of 1α,24-dihydroxyvitamin $D_3$ in the lotion was 2 μg/g) and the lotion of Comparative Example 9 (wherein the content of 1α,24-dihydroxyvitamin $D_3$ in the lotion was 2 μg/g) according to test method 5 are shown in FIG. 2.

What is claimed is:

1. An active vitamin $D_3$ emulsion lotion containing the following components:

(a) a therapeutically effective amount of active vitamin $D_3$, (b) an oil phase component containing a solid oil component comprising white Petrolatum and a higher alcohol and a liquid oil component comprising squalane, (c) an aqueous phase component containing ionic polysaccharide, and (d) nonionic surfactant;

wherein, (1) the content of said ionic polysaccharide is 0.3 to 1.0 parts by weight of the entire preparation, (2) the content of said higher alcohol is 0.2 to 1.0 parts by weight of the entire preparation, and (3) the HLB of said nonionic surfactant is 10 or more.

2. A lotion as set forth in claim 1 wherein the weight ratio of said oil phase component to said aqueous phase component (oil phase component/aqueous phase component) is 15/85 to 3/97.

3. A lotion as set forth in either of claims 1 or 2 wherein the content of said nonionic surfactant is 1.8 to 5.2 parts by weight of the entire preparation.

4. A lotion as set forth in either of claims 1 or 2 wherein said active vitamin $D_3$ is an active vitamin $D_3$ selected from the group consisting of 1α,24-dihydroxyvitamin $D_3$, 1α,25-dihydroxyvitamin $D_3$ and 1α-hydroxyvitamin $D_3$.

5. A lotion as set forth in either of claims 1 or 2 wherein said ionic polysaccharide is xanthane gum and/or carrageenan.

6. A lotion as set forth in either of claims 1 or 2 wherein its viscosity is 500–1400 mPa·s when measured with a Brookfield rotational viscometer using a spindle no. LV4 at 60 rpm and 25° C.

7. A lotion as set forth in either of claims 1 or 2 that is a preparation for treatment of skin disease.

8. A lotion as set forth in claim 7 wherein said in disease is psoriasis or keratosis.

* * * * *